United States Patent [19]

Monnier et al.

[11] 4,412,047

[45] Oct. 25, 1983

[54] CYCLOALIPHATIC DIEPOXIDE, ITS PREPARATION AND ITS USE

[75] Inventors: Charles E. Monnier, Basel; Friedrich Lohse, Oberwil, both of Switzerland

[73] Assignee: Ciba-Geigy Corporation, Ardsley, N.Y.

[21] Appl. No.: 419,690

[22] Filed: Sep. 20, 1982

[30] Foreign Application Priority Data

Oct. 1, 1981 [CH] Switzerland .................... 6352/81

[51] Int. Cl.$^3$ .................... C08G 59/24; C07 303/10
[52] U.S. Cl. .................... 525/507; 525/510; 528/103; 528/361; 528/365; 528/391; 528/406; 528/407; 528/408; 528/409; 528/418; 549/525; 549/545
[58] Field of Search ............... 525/507, 510; 528/103, 528/361, 365, 391, 406, 407, 408, 409, 418; 549/545, 525

[56] References Cited

U.S. PATENT DOCUMENTS

3,065,209  11/1962  Frostick et al. .................... 528/365
3,244,732  4/1966  Frostick et al. .................... 549/545

FOREIGN PATENT DOCUMENTS

793150  4/1958  United Kingdom .

OTHER PUBLICATIONS

E. A. Fehnel, J. Amer. Chem. Soc., 94:11, 3961 (1972).
K. Suga et al, J. Appl. Chem. Biotechnol., 23, 131 (1973).

*Primary Examiner*—Earl A. Nielsen
*Attorney, Agent, or Firm*—Luther A. R. Hall

[57] ABSTRACT

1,5-Dimethyl-1,2;5,6-diepoxycyclooctane is prepared by epoxidizing 1,5-dimethylcycloocta-1,5-diene with aqueous peracetic or perpropionic acid at a temperature not exceeding 50° C. and within a pH range from 1.5 to 5.5.

The diepoxide according to the invention can be cured by means of curing agents for epoxide resins to give moulded materials having valuable mechanical properties. It is also suitable for use as a reactive, latent diluent.

6 Claims, No Drawings

CYCLOALIPHATIC DIEPOXIDE, ITS PREPARATION AND ITS USE

The present invention relates to the cycloaliphatic diepoxide 1,5-dimethyl-1,2;5,6-diepoxycyclooctane, a process for its preparation and its use.

It is known from British Pat. No. 793,150 that cycloocta-1,5-diene can be epoxidised in good yields by means of anhydrous peracetic acid dissolved in an organic solvent. If 1,5-dimethylcycloocta-1,5-diene is used instead of cycloocta-1,5-diene and attempts are made to epoxidise it by the process disclosed in the above British patent, the corresponding diepoxide compound is obtained in a yield of only about 60%, and this compound is contaminated with several by-products, mainly 1,5-dimethylhydroxyacetylcyclooctane 5,6-epoxide.

It has now been found that 1,5-dimethyl-1,2;5,6-diepoxycyclooctane can be prepared in improved yields by epoxidising 1,5-dimethylcycloocta-1,5-diene if the epoxidisation is carried out in aqueous peracetic or perpropionic acid and within a specific pH range.

In comparison with 1,2;5,6-diepoxycyclooctane, which is known and which constitutes a high-melting compound and is relatively reactive in respect of epoxide resin curing agents, 1,5-dimethyl-1,2;5,6-diepoxycyclooctane according to the invention has a low viscosity and is less reactive. In addition to an improved stability on storage, 1,5-dimethyl-1,2;5,6-diepoxycyclooctane has the advantage that it is an excellent latent reactive diluent for epoxide resins. As is known, it is possible to add non-reactive plasticisers or reactive diluents, such as monoepoxides, to epoxide resins in order to reduce their viscosity, but in most cases the mechanical properties of the cured epoxide resins are thereby impaired.

The present invention thus relates to 1,5-dimethyl-1,2;5,6-diepoxycyclooctane, which has the formula

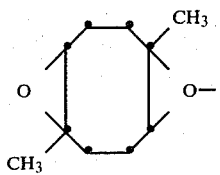

and to a process for its preparation which comprises epoxidising 1,5-dimethylcycloocta-1,5-diene with aqueous peracetic or perpropionic acid at a temperature of not more than 50° C., preferably within a temperature range from 0° to 40° C., and within a pH range from 1.5 to 5.5, preferably from 2 to 4.

It is advantageous to use a 20 to 50% aqueous solution of peracetic acid or perpropionic acid for epoxidising 1,5-dimethylcycloocta-1,5-diene.

It is not necessary to use an excess of peracetic acid or perpropionic acid for epoxidising 1,5-dimethylcycloocta-1,5-diene. In order to keep the formation of by-products as low as possible, it is advisable to employ 1,5-dimethylcycloocta-1,5-diene and the appropriate percarboxylic acid in a molar ratio of 1:2.

The adjustment of the pH of the reaction solution to a specific value is effected by means of a base, preferably sodium hydroxide or potassium hydroxide solution.

In a further preferred embodiment, 1,5-dimethylcyclooctadiene, dissolved in an aprotic solvent, is initially taken and the aqueous solution of per-acid is added dropwise to this organic solution. This procedure offers the advantage that the acetic or propionic acid formed in the epoxidisation can be removed more easily from the organic phase by washing with water.

The aprotic solvents used are the customary solvents, for example chloroform, chlorobenzene or benzene as nonpolar solvents, or dimethylformamide, dimethylacetamide, N-methylpyrrolidone, hexaphosphoric acid triamide or sulfolane as polar, aprotic solvents.

1,5-Dimethylcycloocta-1,5-diene, which is employed in the process according to the invention, is known and can be prepared in accordance with the process described in "Journal of Appl. Chem. Biotechnol., 1973, 23, 131" by dimerisation of isoprene with nickel naphthenate.

1,5-Dimethyl-1,2;5,6-diepoxycyclooctane can be cured with the curing agents which are customary for epoxide resins and produces insoluble, infusible substances having industrially valuable properties. Since 1,5-dimethyl-1,2;5,6-diepoxycyclooctane has a low viscosity, it is preferably used as a latent reactive diluent or as a casting resin, but it can also be used as a laminating resin, for surface-coatings, as a dipping resin, in compression-moulding materials, as an insulating resin for the electrical industry, as a sealing composition or as an adhesive.

If desired, 1,5-dimethyl-1,2;5,6-diepoxycyclooctane can, therefore, also be cured in a mixture with other epoxide resins.

The present invention also relates, therefore, to curable mixtures containing 1,5-dimethyl-1,2;5,6-diepoxycyclooctane and curing agents for epoxide resins and, if desired, also another epoxide resin.

Examples of curing agents which may be mentioned are the conventional curing agents for epoxide resins, including aliphatic, cycloaliphatic, aromatic and heterocyclic amines, such as bis-(4-aminophenyl)-methane, aniline-formaldehyde resin, bis-(4-aminophenyl) sulfone, ethylenediamine, propane-1,2-diamine, propane-1,3-diamine, hexamethylenediamine, diethylenetriamine, triethylenetetramine, 2,2,4-trimethylhexane-1,6-diamine, 2,3,3-trimethylhexane-1,6-diamine, m-xylylenediamine, bis-(4-aminocyclohexyl)-methane, 2,2-bis-(4-aminocyclohexyl)-propane, 2,2-bis-(4-amino-3-methylcyclohexyl)-propane and 3-aminomethyl-3,5,5-trimethylcyclohexylamine (isophoronediamine); polyaminoamides, for example those formed from aliphatic polyamines and dimerised or trimerised fatty acids, polyphenols, such as resorcinol, hydroquinone, 2,2-bis-(4-hydroxyphenyl)-propane, phenol-aldehyde resins and oil-modified phenol-aldehyde resins, phosphoric acid, polythiol, such as the polythiols commercially available under the designation "Thiokols", polycarboxylic acids and anhydrides thereof, for example phthalic anhydride, tetrahydrophthalic anhydride, methylenedomethylenetetrahydrophthalic anhydride, nonenylsuccinic anhydride, dodecenylsuccinic anhydride, hexahydrophthalic anhydride, hexachloroendomethylenetetrahydrophthalic anhydride, hexachloroendomethylenetetrahydrophthalic anhydride and endomethylenetetrahydrophthalic anhydride and mixtures thereof, maleic anhydride, succinic anhydride, pyromellitic anhydride, benzophenone-3,3',4,4'-tetracarboxylic acid dianhydride, polysebacic anhydride and polyazelaic anhydride, the acids of the previously mentioned anhydrides and also isophthalic acid, terephthalic acid, citric acid and mellitic acid. Polycarboxylic acids or anhydrides which are particularly preferred are those which are liquid below 60° C. It is also possible to use curing agents having a catalytic action, for example tertiary amines (for example 2,4,6-tris-(dimethylaminoethyl)-phenol and other Mannich bases, N-benzyldimethylamine and triethanolamine); alkali metal alkoxides of alcohols (for example an Na alcoholate of 2,4-dihydroxy-3-hydroxymethylpentane), tin salts of alkanoic acids (for example tin octanoate) and Friedel-Crafts catalysts, such as boron trifluoride and boron trichloride and complexes and chelate compounds thereof which are obtained by reacting boron trifluoride with, for example, 1,3-diketones.

Together with the curing agents it is also possible to employ suitable curing accelerators. If poly(aminoamides), polythiols or polycarboxylic acid anhydrides are used, it is possible to use as accelerators tertiary amines or salts thereof, quaternary ammonium compounds or alkali metal alkoxides. Examples of specific accelerators are N-benzyldimethylamine, 2,4,6-tris-(dimethylaminomethyl)-phenol, imidazoles and triamylammoniumphenoxide.

Other accelerators which can also be used are, in particular, magnesium nitrate and manganese nitrate, fluorinated and chlorinated carboxylic acids and salts thereof, such as magnesium trifluoroacetate, Na trifluoroacetate, magnesium trichloroacetate, Na trichloroacetate, trifluoromethanesulfonic acid and salts thereof, such as the manganese, zinc, magnesium, nickel and cobalt salts, and magnesium perchlorate and calcium perchlorate.

The quantity of curing agent employed depends on the chemical nature of the curing agent and on the desired properties of the curable mixture and of the cured product. The maximum quantity can be determined easily. If the curing agent is an amine, 0.75 to 1.25 equivalents of amine hydrogen per 1 epoxide equivalent are normally employed. If polycarboxylic acids or their anhydrides are employed, 0.4 to 1.1 equivalents of carboxyl group or anhydride group, respectively, per 1 equivalent of epoxide group are generally used. If polyphenols are used as curing agents, 0.75 to 1.25 phenolic hydroxyl groups are employed per 1 epoxide equivalent. Curing agents having a catalytic activity are generally employed in quantities of 1 to 40 parts by weight per 100 parts by weight of epoxide resin.

Depending on the nature of the curing agent used, the curing can be carried out at room temperature or at elevated temperatures.

If desired, the curing can also be carried out in two stages, for example by interrupting the curing process or, if a curing agent for elevated temperatures is employed, by curing the curable mixture only partially at lower temperatures. The products thus obtained are precondensates which are still fusible and soluble (so-called "B-stage resins") and are suitable for compression-moulding materials, sintering powders or prepregs.

The most suitable of the epoxide resins which can be used as a mixture with 1,5-dimethyl-1,2;5,6-diepoxycyclooctane are the cycloaliphatic epoxides resins, for example vinylcyclohexane dioxide, limonene dioxide, dicyclopentadiene dioxide, 3,4-epoxydihydrodicyclopentadienyl glycidyl ether, the bis-(3,4-epoxydihydrodicyclopentadienyl) ether of ethylene glycol, 3,4-epoxycyclohexylmethyl 3',4'-epoxycyclohexanecarboxylate and its 6,6'-dimethyl derivative, ethylene glycol bis-(3,4-epoxycyclohexanecarboxylate), the acetal formed from 3,4-epoxycyclohexanecarboxyaldehyde and 1,1-bis-(hydroxymethyl)-3,4-epoxycyclohexane, and bis-(2,3-epoxycyclopentyl) ether.

Furthermore, the polyglycidyl and poly-(β-methylglycidyl) esters obtainable by reacting polycarboxylic acids with epichlorohydrin, glycerol dichlorohydrin or β-methylepichlorohydrin, in the presence of alkali, are also suitable for the preparation of epoxide resin mixtures. The polyglycidyl esters can be derived from aliphatic carboxylic acids, for example oxalic acid, succinic acid or adipic acid, sebacic acid, dimerised or trimerised linoleic acid, cycloaliphatic carboxylic acids, such as hexahydrophthalic acid, 4-methylhexahydrophthalic acid, tetrahydrophthalic acid and 4-methyltetrahydrophthalic acid, or aromatic carboxylic acids, such as phthalic acid, isophthalic acid or terephthalic acid.

Other epoxide resins with which 1,5-dimethyl-1,2;5,6-diepoxycyclooctane can be used are the polyglycidyl ethers and poly-(β-methylglycidyl) ethers which are obtained by reacting compounds containing more than one alcoholic or phenolic hydroxyl group with epichlorohydrin, glycerol dichlorohydrin or β-methylepichlorohydrin under alkaline conditions or in the presence of an acid catalyst followed by subsequent alkaline treatment. Such polyglycidyl ethers can be derived from aliphatic alcohols, for example ethylene glycol and poly-(oxyethylene) glycols, such as diethylene glycol and triethylene glycol, propylene glycol and poly-(oxypropylene) glycols, propane-1,3-diol, butane-1,4-diol, pentane-1,5-diol, hexane-1,6-diol, hexane-2,4,6-triol, glycerol, 1,1,1-trimethylolpropane and pentaerythritol, from cycloaliphatic alcohols, such as quinitol, 1,1-bis-(hydroxymethyl)-cyclohex-3-ene, bis-(4-hydroxycyclohexyl)-methane and 2,2-bis-(4-hydroxycyclohexyl)-propane, or from alcohols containing an aromatic nucleus, such as N,N-bis-(2-hydroxyethyl)-aniline and 4,4'-bis-(2-hydroxyethylamino)-diphenylmethane. Preferred polyglycidyl ethers are those which are derived from compounds containing two or more phenolic hydroxyl groups per molecule, such as resorcinol, catechol, hydroquinone, bis-(4-hydroxyphenyl)-methane, 1,1,2,2-tetrakis-(4-hydroxyphenyl)-ethane, 4,4'-dihydroxydiphenyl, bis-(4-hydroxyphenyl) sulfone and, in particular, phenolformaldehyde or cresol-formaldehyde novolac resins, 2,2-bis-(4-hydroxyphenyl)-propane (bisphenol A) and 2,2-bis-(3,5-dibromo-4-hydroxyphenyl)-propane.

It is also possible to use, for the preparation of the epoxide resin mixtures, poly-(N-glycidyl) compounds which are obtained by dehydrochlorinating reaction products formed from epichlorohydrin and amines having at least two amine hydrogen atoms, such as aniline, n-butylamine, bis-(4-aminophenyl)-methane, bis-(4-aminophenyl) sulfone and bis-(4-methylaminophenyl)-methane. Further poly-(N-glycidyl) compounds which can be employed are triglycidyl isocyanurate, N,N'-diglycidyl compounds of cyclic alkyleneureas, such as ethyleneurea and 1,3-propyleneurea, and N,N'-diglycidyl compounds of hydantoins, such as 5,5-dimethylhydantoin.

The curable mixtures according to the invention can, in addition, also contain plastisizers, such as dibutyl phthalate, dioctyl phthalate or tricresyl phosphate, or additives, such as fillers, reinforcing agents, dyes, flow assistants, flame-retarding substances and mould-release agents. Examples of suitable extenders, fillers and reinforcing agents are asbestos, asphalt, bitumen, glass fibres, textile fibres, carbon fibres, boron fibres, mica, alumina, gypsum, titanium dioxide, chalk, quartz powder, cellulose, kaolin, ground dolomite, wollastonite, silica having a large specific surface area (obtainable under the tradename "Aerosil"), alumina which has been modified with long-chain amines (obtainable under the tradename "Bentone"), powdered polyvinyl chloride, polyolefins or aminoplasts, and metal powders, such as aluminium or iron powder. Fireproofing agents, such as antimony trioxide, can also be added to the curable mixtures.

The examples which follow describe the invention. Unless there is a note to the contrary, parts are parts by weight.

EXAMPLE 1

20.44 g (0.15 mol) of 1,5-dimethylcycloocta-1,5-diene and 90 ml of chloroform are initially placed in a 350 ml sulfonation flask, equipped with a stirrer, a thermometer, a condenser, a pH meter with an electrode and a dropping funnel. The mixture is warmed to about 50° C. and 115.71 g (0.31 mol) of 28% aqueous perpropionic acid are added dropwise in the course of about 2.5 hours, the pH being kept at pH 4.0 with 20% NaOH.

After completion, the reaction mixture is kept at this temperature for 1 hour and the organic phase is then washed once with approximately 100 ml of 1 N NaOH and several times with water, dried over sodium sulfate and concentrated in vacuo. This gives 22.98 g (91.07% of theory) of a colourless liquid containing, by gas chromatography, 76.96% of 1,5-dimethyl-1,2;5,6-diepoxycyclooctane. 15.05 g of the crude product are chromatographed over approximately 100 g of silica gel, petroleum ether/ether (mixed in the ratio of 60:40) being used to elute 6.35 g of pure diepoxide, which is distilled at 52°–55° C./106.6 Pa.

IR spectrum (film): 2,980–2,960, 1,470, 1,450, 1,390, 1,070 cm$^{-1}$.

NMR spectrum (CDCl$_3$): 1.30 ppm s 6H (methyl—); 1.8–2.0 ppm s br. 8H (cycl—CH$_2$—); 3.6–3.8 ppm m 2H (cycl—CH—).

| Elementary analysis: | | C$_{10}$H$_{16}$O$_2$ (168.24) | |
|---|---|---|---|
| calculated: | C 71.39% | found: | C 71.7% |
| | H 9.59% | | H 9.8% |
| | O 26.41% | | O 26.30% |

EXAMPLE 2

10.22 g (0.075 mol) of 1,5-dimethylcycloocta-1,5-diene and 45 ml of chloroform are initially placed in a 200 ml sulfonation flask equipped with a stirrer, a thermometer, a condenser, a pH meter with an electrode and a dropping funnel. The mixture is kept at 25° C. and a total of 30.4 g (0.16 mol) of 40% aqueous peracetic acid are added dropwise in the course of 2.5 hours, the pH being kept at pH 4.0 with 20% NaOH. After completion, the mixture is kept at this temperature for a further 30 minutes and the organic phase is then washed once with approximately 150 ml of 1 N NaOH and several times with water, dried over sodium sulfate and concentrated in vacuo. This gives 10.32 g (81% of theory) of a colourless, slightly viscous liquid, which is analysed by gas chromatography and contains 82.63% of 1,5-dimethyl-1,2;5,6-diepoxycyclooctane, which, as in Example 1, is obtained in a pure state by distillation.

EXAMPLE 3

6.81 g (0.05 mol) of 1,5-dimethylcycloocta-1,5-diene in 20 ml of chloroform and 40 ml of water are initially placed in a 100 ml sulfonation flask equipped with a stirrer, a thermometer, a condenser, a pH meter with an electrode, a dropping funnel and a Dosimat fitted with an Impulsomat (made by METRON) for the addition of NaOH. A total of 20.27 g (0.107 mol) of 40% aqueous peracetic acid is added dropwise in the course of about 3 hours at 22°–25° C. and at a specific pH, samples being taken periodically and examined by gas chromatography. When the dropwise addition is complete, the reaction mixture is stirred for about a further 45 minutes and is then transferred to a drop funnel and the aqueous phase is extracted 3 times with chloroform and worked up as in Example 2. The product is analysed by gas chromatography, the following yields, relating to the crude yield, of 1,5-dimethyl-1,2;5,6-diepoxycyclooctane being obtained:

at pH 2: 79%,
at pH 3: 82%,
at pH 4: 76% and
at pH 5: 76%.

USE EXAMPLES

Example I

Portions of 100 parts of 1,5-dimethyl-1,2;5,6-diepoxycyclooctane and of 100 parts of 1,2;5,6-diepoxycyclooctane are each mixed with 10 parts of BF$_3$-monoethylamine as curing agent. Differential thermoanalysis is used to determine, firstly the reactivity of these mixtures and, secondly, the glass transition temperature of the cured products.

(a) Thermal analysis

Differential thermal analysis (DTA) is used to determine the reactivity. Approximately 20 mg of the resin-curing agent mixture are warmed at a heating rate of 4° C./minute in a small Al crucible in the measuring chamber of a DTA apparatus (TA-2000 made by METTLER-Instrumente AG, Griefensee, Switzerland), and the temperature difference compared with an empty crucible warmed at the same time is recorded continuously. The temperatures for the start of the reaction ($T_B$), for the maximum reaction rate ($T_{RG\ max}$) and for the end of the reaction ($T_E$) are read off from the curve thus obtained as parameters characterising the reactivity. The experimental results are quoted in Table 1.

(b) Determination of the glass transition temperatures (GTT)

4 g portions of the resin-curing agent mixture are poured into a thin-walled Al crucible of a diameter of about 5 cm and are cured therein. A sample of the disc thus obtained is withdrawn in order to determine the glass transition temperature of the crosslinked polymer with the aid of differential thermal analysis. The specific heat changes at the transition point; this change is registered as a point of inflection in the curve recorded by the DTA instrument (TA-200 made by METTLER-Instrumente AG, Griefensee, Switzerland). The glass transition temperature enables conclusions to be drawn regarding the heat distortion point of the polymer obtained. The figures determined are quoted in Table 1.

TABLE 1

| Mixture | 100 parts of 1,5-dimethyl-1,2;5,6-diepoxycyclooctane and 10 parts of BF₃—monoethylamine | 100 parts of 1,2;5,6-diepoxycyclooctane and 10 parts of BF₃—monoethylamine |
|---|---|---|
| Thermal analysis | | |
| $T_B$ (°C.) | 74 | 48 |
| $T_{RG\ max}$ (°C.) | 123 | 113 |
| $T_E$ (°C.) | 239 | 184 |
| Curing | 6 hours at 120° C. and 6 hours at 180° C. | |
| GTT (°C.) | 139 | 88 |

Example II 100 parts of 1,5-dimethyl-1,2;5,6-diepoxycyclooctane are mixed with 182 parts of phthalic anhydride. The reactivity of this mixture and the glass transition temperature (GTT) of the cured moulding are determined as in Example I.

Thermal analysis:
$T_B$ (°C.) 100
$T_{RG\ max}$ (°C.) 183
$T_E$ (°C.) 267
Curing: 6 hours at 120° C. and 6 hours at 180° C.
GTT (°C.) 123.

What is claimed is:

1. 1,5-Dimethyl-1,2;5,6-diepoxycyclooctane.
2. A process for the preparation of 1,5-dimethyl-1,2;5,6-diepoxycyclooctane according to claim 1, which comprises epoxidising 1,5-dimethylcycloocta-1,5-diene with aqueous peracetic or perpropionic acid at a temperature not exceeding 50° C. and within a pH range from 1.5 to 5.5.
3. A process according to claim 2, wherein a 20% or 50% aqueous solution of peracetic acid or perpropionic acid is used.
4. A process according to claim 2, wherein the molar ratio of 1,5-dimethylcycloocta-1,5-diene to peracetic or perpropionic acid is 1:2.
5. A process according to claim 2, wherein the epoxidisation of 1,5-dimethylcycloocta-1,5-diene is effected within the pH range from 2 to 4.
6. A curable mixture containing 1,5-dimethyl-1,2:5,6-diepoxycyclooctane according to claim 1 and a curing agent for epoxide resins and optionally a further epoxide resin.

* * * * *